United States Patent
Homyk et al.

(10) Patent No.: US 10,722,177 B2
(45) Date of Patent: Jul. 28, 2020

(54) CARDIOVASCULAR MONITORING USING COMBINED MEASUREMENTS

(71) Applicant: Verily Life Sciences LLC, Mountain View, CA (US)

(72) Inventors: Andrew Homyk, Belmont, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1122 days.

(21) Appl. No.: 14/974,894

(22) Filed: Dec. 18, 2015

(65) Prior Publication Data

US 2017/0172510 A1 Jun. 22, 2017

(51) Int. Cl.
*A61B 8/00* (2006.01)
*A61B 5/00* (2006.01)
*A61B 5/0402* (2006.01)
*A61B 5/04* (2006.01)
(Continued)

(52) U.S. Cl.
CPC .......... *A61B 5/721* (2013.01); *A61B 5/0004* (2013.01); *A61B 5/0024* (2013.01);
(Continued)

(58) Field of Classification Search
None
See application file for complete search history.

(56) References Cited

U.S. PATENT DOCUMENTS

2014/0221849 A1  8/2014  Farringdon et al.
2014/0249431 A1*  9/2014  Banet ............... A61B 5/01
                                          600/485
(Continued)

FOREIGN PATENT DOCUMENTS

WO   WO 2015/101947 A2   7/2015

OTHER PUBLICATIONS

International Search Report issued in co-pending International Patent Application No. PCT/US2016/064097, European Patent Office, dated Mar. 10, 2017, 4 pages.
(Continued)

*Primary Examiner* — Joel F Brutus
(74) *Attorney, Agent, or Firm* — McDonnell Boehnen Hulbert & Berghoff LLP (57) ABSTRACT

A system for collecting data for assessment of cardiovascular function includes a plurality of monitoring devices coupled to different respective body parts. Each monitoring device is configured to measure a respective signal at the respective body part in response to cardiovascular activity. The respective signal includes a cardiovascular component attributable to the cardiovascular activity and an artifact component not attributable to the cardiovascular activity. When the monitoring devices measure the respective signals simultaneously over a same time period, the cardiovascular components are correlated, and the artifact components are not correlated. The system also includes a controller configured to: identify the cardiovascular components included in the signal measurements, according to the correlation of the cardiovascular components; reject the artifact components included in the signal measurements, according to the non-correlation of the artifact components; and determine cardiovascular information from the identified cardiovascular components for an assessment of cardiovascular function.

8 Claims, 6 Drawing Sheets

(51) Int. Cl.
*A61B 5/0295* (2006.01)
*A61B 8/08* (2006.01)
*A61B 5/026* (2006.01)
*A61B 5/11* (2006.01)
*A61B 5/024* (2006.01)
*A61B 8/06* (2006.01)

(52) U.S. Cl.
CPC .......... *A61B 5/0261* (2013.01); *A61B 5/0295* (2013.01); *A61B 5/02416* (2013.01); *A61B 5/0402* (2013.01); *A61B 5/04012* (2013.01); *A61B 5/11* (2013.01); *A61B 5/7246* (2013.01); *A61B 5/7285* (2013.01); *A61B 8/0883* (2013.01); *A61B 8/4416* (2013.01); *A61B 8/5269* (2013.01); *A61B 8/06* (2013.01); *A61B 8/488* (2013.01); *A61B 2562/06* (2013.01)

(56) References Cited

U.S. PATENT DOCUMENTS

2014/0275852 A1 9/2014 Hong et al.
2015/0282718 A1 10/2015 Wiard et al.

OTHER PUBLICATIONS

Written Opinion issued in co-pending International Patent Application No. PCT/US2016/064097, European Patent Office, dated Mar. 10, 2017, 8 pages.

Wijshoff, R., et al. "PPG motion artifact handling using a self-mixing interferometric sensor," Optical Fibers, Sensors, and Devices for Biomedical Diagnostics and Treatment XI, vol. 7894 (2011).

Wijshoff R., et al. "Reducing motion artifacts in photoplethysmograms by using relative sensor motion: phantom study", J. Biomed. Opt., vol. 17, No. 11, (2012).

Bruser, C., et al., "Adaptive Beat-to-Beat Heart Rate Estimation in Ballistogradiograms," IEEE Transactions on Information Technology in Biomedicine, vol. 15, No. 15 (2011).

Ebrahim, M.H., "A Robust Senor Fusion Method for Heart Rate Estimation," J. Clin Monit, vol. 6, p. 385-393 (1997)—Abstract Only.

Li, Q., "Robust heart rate estimation from multiple asynchronous noisy sources using signal quality indices and a Kalman filter," Physiological Measurement, Vo. 29, No. 1, p. 15-32 (2008).

\* cited by examiner

CARDIOVASCULAR MONITORING USING COMBINED MEASUREMENTS

BACKGROUND

Unless otherwise indicated herein, the materials described in this section are not prior art to the claims in this application and are not admitted to be prior art by inclusion in this section.

Heart disease remains one of the leading causes of death in developed nations. For many cases of heart disease, mortality and morbidity may be avoided by early detection and treatment. As such, frequent monitoring of the cardiovascular system may improve health and quality of life for a vast number of individuals.

SUMMARY

Example systems can robustly and accurately collect data relating to a subject's cardiovascular function. The example systems may include monitoring devices that measure signals relating to pulse, blood flow, blood pressure, and/or other indicators of cardiovascular function. The monitoring devices, however, may also measure artifacts that are not related to cardiovascular function. Such artifacts may obscure, distort, or misrepresent data relating to the cardiovascular function. The example systems can extract cardiovascular data from the measurements and separate the cardiovascular data from the artifacts. The extracted cardiovascular data can then be used for an accurate assessment of the cardiovascular function.

In an example embodiment, a system for collecting data for assessment of cardiovascular function includes a plurality of monitoring devices configured to be coupled to different respective body parts of a subject. Each monitoring device includes a respective first communication interface and is configured to measure a respective signal at the respective body part in response to cardiovascular activity. The respective signal includes a cardiovascular component attributable to the cardiovascular activity and an artifact component not attributable to the cardiovascular activity. In response to the monitoring devices measuring the respective signals simultaneously over a same time period, the cardiovascular components included in the signal measurements by the monitoring devices are correlated, and the artifact components included in the signal measurements by the monitoring devices are not correlated. The system also includes a controller. The controller includes a second communication interface configured to be communicatively coupled to the first communication interface of each monitoring device. The controller also includes at least one data storage device. Additionally, the controller includes at least one processor configured to: (i) receive the signal measurements from the monitoring devices via the second communication interface; (ii) store the signal measurements on the at least one data storage device; (iii) identify the cardiovascular components included in the signal measurements, according to the correlation of the cardiovascular components; (iv) reject the artifact components included in the signal measurements, according to the non-correlation of the artifact components; and (v) determine cardiovascular information from the identified cardiovascular components for an assessment of cardiovascular function.

In another example embodiment, a method for collecting data for assessment of cardiovascular function includes measuring, with each of a plurality of monitoring devices coupled to different respective body parts of a subject, a respective signal at the respective body part in response to cardiovascular activity occurring during a same time period. The respective signal includes a cardiovascular component attributable to the cardiovascular activity and an artifact component not attributable to the cardiovascular activity. The method also includes storing, in at least one data storage device, the signal measurements by the monitoring devices. Additionally, the method includes identifying, with at least one processor, the cardiovascular components in the signal measurements according to a correlation of the cardiovascular components. Furthermore, the method includes rejecting, with the at least one processor, the artifact components included in the signal measurements according to a non-correlation of the artifact components. The method also includes determining cardiovascular information from the identified cardiovascular components.

In yet another embodiment, a system for collecting data for assessment of cardiovascular function includes a first monitoring device configured to measure a first signal in response to cardiovascular activity during a time period. The first signal includes data relating to a plurality of cardiac cycles during the time period, the first monitoring device including a first communication interface. The system also includes a second monitoring device configured to measure a second signal in response to the cardiovascular activity during the time period. The second monitoring device including a second communication interface. Additionally, the system includes a controller. The controller includes a third communication interface configured to be communicatively coupled to the first communication and second communication interfaces. The controller also includes at least one data storage device. Furthermore, the controller includes at least one processor configured to: (i) receive, via the third communication interface, the measurement of the first signal from the first monitoring device and the measurement of the second signal from the second monitoring device; (ii) determine cardiac cycle information from the data in the first signal; and (iii) determine further cardiovascular information from the measurement of the second signal based on the cardiac cycle information.

These as well as other aspects, advantages, and alternatives, will become apparent to those of ordinary skill in the art by reading the following detailed description, with reference where appropriate to the accompanying drawings.

While the invention is susceptible to various modifications and alternative forms, specific embodiments have been shown by way of example in the Figures and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims. It should be understood that other embodiments may include more or less of each element shown in a given Figure. Further, some of the illustrated elements may be combined or omitted. Yet further, an example embodiment may include elements that are not illustrated in the Figures.

DETAILED DESCRIPTION

The following detailed description describes various features and functions of the disclosed systems and methods with reference to the accompanying figures. In the Figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Overview

Heart disease remains one of the leading causes of death in developed nations. For many cases of heart disease, mortality and morbidity may be avoided by early detection and treatment. As such, frequent monitoring of the cardiovascular system may improve health and quality of life for a vast number of individuals.

Example systems can robustly and accurately collect data relating to a subject's cardiovascular function. The example systems include cardiovascular monitoring devices that may collect data relating to pulse, blood flow, blood pressure, and/or other indicators of cardiovascular function. The cardiovascular monitoring devices may be coupled to different parts of the subject's body.

Motion of the body parts during data collection can introduce motion-related artifacts into the collected data. In other words, the cardiovascular monitoring devices may detect signals that result from the motion of the body parts. Motion-related artifacts may obscure, distort, or misrepresent the actual cardiovascular data.

In addition to motion-related artifacts, the data collected by the monitoring devices may include other types of artifacts. Unless the artifacts can be identified and filtered from the collected data, the collected data may not provide accurate information for the assessment of cardiovascular function.

Advantageously, the example systems can process the collected data to allow cardiovascular function to be accurately evaluated, even if the collected data may include artifacts. In particular, the example systems may collect data simultaneously from multiple monitoring devices. The data from these monitoring devices are based on measurements of indicators resulting from the same cardiac activity. The data from the monitoring devices include components that reflect common aspects of the same cardiac activity. As such, the data include components that are correlated. By statistically comparing the data collected from the multiple cardiovascular monitoring devices during the same time period, the example system can identify the correlated components which are attributable to cardiovascular function.

The data from the monitoring devices may also include components that reflect the measurement of artifacts. In contrast to the correlated cardiovascular components, the artifact components may generally be the result of different respective phenomena. For instance, motion-related artifacts may be caused by different motions by different respective body parts. Additionally, artifacts may also result from the operation of a particular type of sensor and the specific type of technology used by that sensor. Thus, the artifact components are generally uncorrelated. Because the artifact components are generally uncorrelated, the process of extracting the correlated cardiovascular components also results in the rejection of the uncorrelated artifact components.

According to example embodiments, cardiac cycle information, e.g., pulsatile waveforms, can be accurately determined from the correlated cardiovascular components. The measurements of electrical activity, changes in blood volume, and/or blood flow can be accurately evaluated with this cardiac cycle information. The cardiac cycle information may also be employed to improve the calculations of other cardiovascular indicators.

In general, one or more monitoring devices may be employed to accurately determine cardiac cycle information to enhance the assessment of cardiovascular function. According to some embodiments, the cardiac cycle information may be used as a reference signal to process data collected by another monitoring device. According to further embodiments, the cardiac cycle information may be used to synchronize data collected by another monitoring device during the same time period. According to yet further embodiments, the cardiac cycle information may be used to optimize, calibrate, or otherwise adjust how data is collected by another monitoring device.

II. Example Embodiments for Collecting Data

Figure 1:
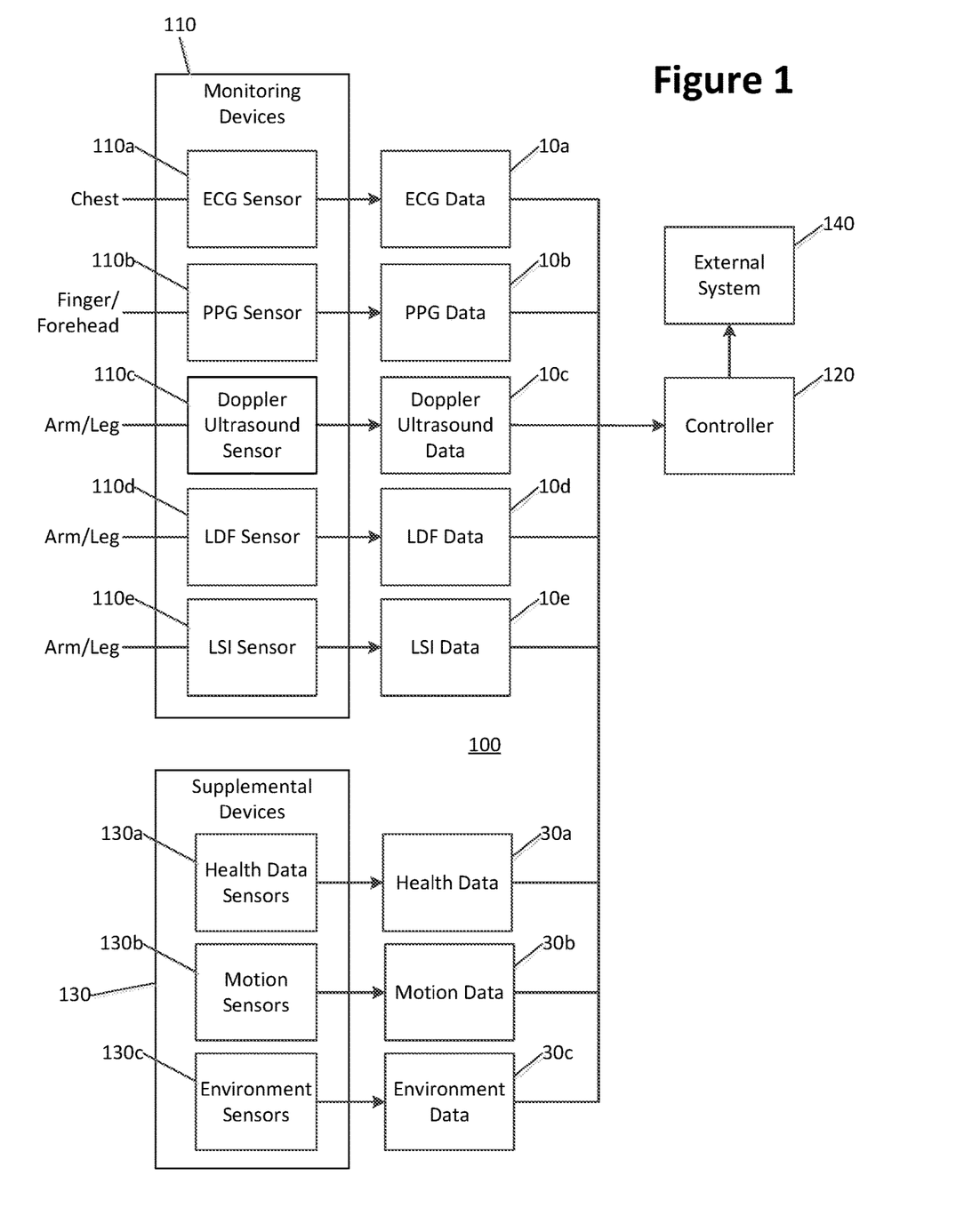
FIG. 1 illustrates an example system that can collect and process data relating to a subject's cardiovascular function, according to aspects of the present disclosure.

FIG. 1 illustrates an example system 100 that can robustly and accurately collect data relating to a subject's cardiovascular function. The example system 100 includes cardiovascular monitoring devices 110 that may collect data relating to pulse, blood flow, blood pressure, and/or other indicators of cardiovascular function. For instance, as shown in FIG. 1, the cardiovascular monitoring devices 110 may include: (i) an electrocardiography (ECG) sensor 110a; (ii) a photoplethysmography (PPG) sensor 110b; (iii) and at least one of a Doppler ultrasound sensor 110c, a laser Doppler flowmetry (LDF) sensor 110d, or a laser speckle imaging (LSI) sensor 110e.

The example system 100 may employ the ECG sensor 110a to collect data 10a relating to electrical activity in the subject's heart. The ECG sensor 110a may include electrodes that are placed, for instance, on the subject's chest. The electrodes detect electrical signals on the skin that arise as the heart experiences a pattern of depolarization/repolarization during each cardiac cycle. Depolarization corresponds to contraction of a heart muscle and occurs when an electrical impulse causes ions to move across heart cell membranes. Repolarization corresponds to relaxation of heart muscle and occurs when the ions return to a resting state. The heart generally experiences a repeating cycle of atrial depolarization, atrial repolarization, ventricular depolarization, and ventricular repolarization. The ECG data 10a provides information on the pattern of depolarization/repolarization over repeating cardiac cycles. A tracing of the ECG data 10a, for instance, may show the pattern as a series of waves including a P wave corresponding to the atrial depolarization, QRS wave corresponding to the ventricular depolarization, and a T wave corresponding to the ventricular repolarization.

The example system 100 may employ the PPG sensor 110b to collect data 10b relating to changes in blood volume in a body part as the subject's heart pumps blood. The photoplethysmography (PPG) sensor 110b may employ a pulse oximeter, which includes a light source, such as a light-emitting diode (LED), and a photodetector, such as a photodiode. The light source illuminates tissue and the photodetector measures the light intensity after the light passes through the tissue. In some embodiments, for instance, the PPG sensor 110b may be coupled to the subject's finger. In such cases, the light source is disposed on one side of the finger and the photodetector is disposed on an opposing side of the finger. The photodetector detects light from the light source after it passes from one side of the finger to the other.

In other embodiments, for instance, the PPG sensor 110b may be coupled to the subject's forehead. Thus, the light source and the photodetector are disposed on the same side of the body part. The photodetector detects light from the light source after it enters the forehead and is reflected back to the surface by tissue in the forehead.

With each cardiac cycle, the heart pumps blood to the finger or forehead to increase blood volume. This change in blood volume increases the optical density of the tissue and, to a lesser degree, lengthens the path for the light travelling from the light source to the photodetector. Thus, with each pulse of blood, more light is absorbed by the tissue and the photodetector measures less light intensity. The measurements of light intensity change in response to the pumping of the heart over repeating cardiac cycles. Thus, the PPG data 10b provides information relating to the blood volume in the body part based on these measurements of light intensity. For instance, the measured signals include a DC component that is attributable to the bulk absorption and scattering of the tissue and an AC component that is directly attributable to variation in blood volume caused by the pressure pulse of the repeating cardiac cycles. The height of the AC component in the resulting waveform is proportional to the pulse pressure, i.e., the difference between the systolic and diastolic pressure in the arteries. In addition to determining changes in blood volume in a body part, the pulse oximeter can also be used to determine oxygen level (or oxygen saturation) in the blood.

The example system 100 may employ at least one of at least one of the Doppler ultrasound sensor 110c, the LDF sensor 110d, or the LSI sensor 110e to collect respective data 10c, 10d, 10e relating to blood flow through blood vessels. The Doppler ultrasound sensor 110c may include an ultrasound transducer that sends sound waves into tissue and detects the sound waves after they have been reflected by blood cells in blood vessels of the tissue. The movement of blood cells causes a change in pitch of the reflected sound waves (the Doppler effect). Thus, the data 10c collected by the Doppler ultrasound sensor 110c includes measurements of blood flow based on the measurement of the reflected sound waves.

The LDF sensor 110d may include one or more laser light sources and a photodetector, such as a photodiode. In an example homodyne system, a laser beam from a light source is directed at the tissue. Some photons in the beam penetrate the tissue and are reflected by moving blood cells in the blood vessels; these photons are Doppler shifted. Simultaneously, other photons reflect from the surface or other relatively static elements of the tissue and experience minimal Doppler shifts. The reflected photons impinge on the photodetector. The electric field at the photodetector results from photons that travel over multiple different paths. The intensity of the light at the photodetector fluctuates with beat frequencies between all of the different combinations of reflected photons, which corresponds to a Doppler spectrum. As the beat frequencies between two Doppler-shifted photons may be detected, the spectrum may be distorted to some extent from a pure Doppler spectrum.

In an example heterodyne system, a laser beam from a light source is split into a reference beam and an illumination beam, e.g., by a beamsplitter, partially reflective mirror, acousto-optic modulator (AOM), etc. Optionally, the frequency of the reference beam can be shifted with an AOM or other phase modulator. The illumination beam is directed to the tissue. Some photons in the illumination beam are reflected by moving blood cells in the blood vessels, and accrue a Doppler shift, while others scatter of quasi-static elements of the tissue and experience minimal Doppler shifts. The reflected photons are combined with the reference beam. The intensity of the light at the photodetector is detected as: (1) the beat frequencies between all of the different combinations of reflected photons, similar to the homodyne system above, and (2) the beat frequencies between the photons of the reference beam (having no Doppler shift, or a fixed offset) and the Doppler-shifted photons. The former produces a distorted Doppler spectrum similar to the homodyne system above; the latter produces a pure Doppler spectrum. When the reference beam does not have an offset, the pure Doppler spectrum is overlayed with the distorted Doppler spectrum, but may have higher magnitude if the reference beam is made sufficiently strong. On the other hand, when the frequency of the reference beam is optionally shifted with an AOM or other phase modulator, the pure Doppler spectrum occurs at an offset frequency (electrically) and can be readily filtered. Using a frequency-shifted reference beam also allows forward and backward flow to be distinguished.

The LDF sensor 110d processes the detected Doppler spectrum(s) produced by the photons that are Doppler shifted when reflected by the moving blood cells. Thus, the data 10d collected by the LDF sensor 110d includes measurements of blood flow based on the Doppler spectrum(s).

The LSI sensor 110e may include one or more laser light sources and a photodetector, such as a photodiode. The laser light source(s) direct coherent light at blood cells in a blood vessel. When the coherent light interacts with the blood cells, the photodetector receives light that scatters from varying positions within the blood vessel and travels a distribution of distances. This results in constructive and destructive interference that varies with the arrangement of the blood cells relative to the photodetector. When the scattered light is imaged, the interference shown in the image varies randomly in space, producing a randomly varying intensity pattern known as speckle. The movement of the blood cells causes fluctuations in the interference, which appear as intensity variations at the photodetector. The temporal and spatial statistics of this speckle pattern provide data relating to the motion of the blood cells. Thus, the data 10e collected by the LSI sensor 110e includes measurements of blood flow based on the analysis of speckle patterns.

The Doppler ultrasound sensor 110c, the LDF sensor 110d, or the LSI sensor 110e may be coupled to the subject's arm or leg. In general, any combination of the sensors 110c-e may be employed to collect information relating to changes in blood flow resulting from the pumping of the heart over repeating cardiac cycles.

Although the cardiovascular monitoring devices 110 shown in FIG. 1 may include the ECG sensor 110a, the PPG sensor 110b, the Doppler ultrasound sensor 110c, the LDF sensor 110d, and the LSI sensor 110e, the cardiovascular monitoring devices 110 may additionally or alternatively include other types of sensors that employ any number of different technologies to measure indicators of cardiovascular function. Additional technologies include, but are not limited to, magnetic resonance imaging (MRI), ultrasonic echocardiography, tonometry, sphygmomanometry, and impedance cardiography.

Figure 2:
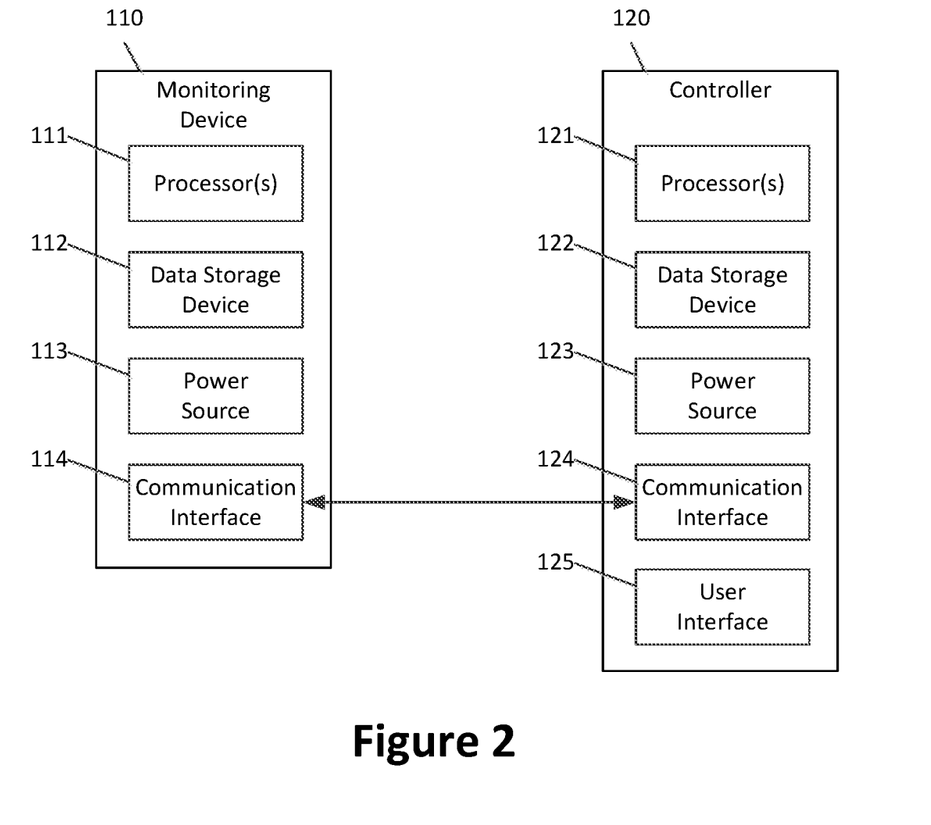
FIG. 2 illustrates an example monitoring device and controller for collecting and processing data relating to a subject's cardiovascular function, according to aspects of the present disclosure.

As shown in FIG. 2, each cardiovascular monitoring device 110 may include at least one processor 111, at least one data storage device 112, a power source 113, and a communication interface 114. The at least one processor 111 manages the general operation of the cardiovascular monitoring device 110 to collect data relating to pulse, blood flow, blood pressure, and/or other indicators of cardiovascular function. The at least one data storage device 113 may include non-volatile memory, such as flash memory, to store the data collected by the cardiovascular monitoring device 110. The power source 113, such as a disposable or rechargeable battery, powers the general operation of the motion sensor device 110.

As FIG. 1 illustrates, the example system 100 also includes a controller 120. The sensors 110a-e transmit the respective data 10a-e to the controller 120 for processing. As shown in FIG. 2, the controller 120 includes at least one processor 121, at least one data storage device 122, a power source 123, at least one communication interface 124, and a user interface 125. The at least one data storage device 122 may store program instructions that can be executed by the at least one processor 121 to manage and process the collection of data by the cardiovascular monitoring devices 110.

The at least one communication interface 124 allows the controller 120 to be communicatively coupled to each cardiovascular monitoring device 110 via the respective communication interface 114. For instance, the controller 120 can communicate with one or more of the cardiovascular monitoring devices 110, for example using a BLUETOOTH® or BLUETOOTH® LOW ENERGY (BLE) (2.4 to 2.485 GHz UHF) wireless connection. Additionally or alternatively, the controller 120 can communicate with one or more of the cardiovascular monitoring devices 110 using a WIFI™ (IEEE 802.11) wireless connection. Additionally or alternatively, the controller 120 can communicate with one or more of the cardiovascular monitoring devices 110 via wired connection.

The controller 120 can signal the cardiovascular monitoring devices 110 via the communication interfaces 114, 124 to collect data. The controller 120 can specify particular modes for data collection. The modes can determine when the data collection should take place (e.g., period of time) and/or how frequently the data should be collected. The modes can determine which of the available cardiovascular monitoring devices 110 should be activated to collect data and what data should be collected.

In response to the controller 120, the cardiovascular monitoring devices 110 collect data relating to cardiovascular function, as described above. Each cardiovascular monitoring device 110 may store the collected data on the at least one data storage device 112 at least temporarily, and the data may be subsequently transmitted to the controller 120 via the communication interfaces 114, 124. The controller 120 may then store the collected data from the cardiovascular monitoring devices 110 on the at least one data storage device 122. The controller 120 may also process the collected data for visual or other presentation on the user interface 125.

To allow the controller 120 to temporally associate the data from the several cardiovascular monitoring devices 110, the collected data may be time-aligned with high precision. For example, the collected data may be time-aligned at ±1 millisecond precision to allow for accurate temporal association. Accordingly, the example system 100 may employ a network time protocol (NTP) to synchronize the cardiovascular monitoring devices 110. In some cases, the controller 120 is employed to synchronize the cardiovascular monitoring devices 110 with an NTP server. Alternatively, each cardiovascular monitoring device 110 may communicate separately with a common NTP server via the respective communication interface 114.

Additionally or alternatively, the collected data may be time-aligned with an event that is detected by each cardiovascular monitoring device 110. In one example, if the cardiovascular monitoring devices 110 also include light sensors, the light sensors may detect the same illumination event, such as room lights being turned on. Thus, the data collected from each cardiovascular monitoring device 110 includes this illumination event, which can be used to time-align the data from all the cardiovascular monitoring devices 110. In another example, the controller 120 may emit a signal, e.g., over a wireless communication channel, that the cardiovascular monitoring devices 110 can detect. Thus, the data collected from each cardiovascular monitoring device 110 includes this emitted signal, which can be used to time-align the data from all the cardiovascular monitoring devices 110.

The controller 120 may be a device that is structurally separate from the cardiovascular monitoring devices 110. For instance, the controller 120 may be conveniently worn by the subject as a wrist-worn device. As such, the subject can conveniently control the cardiovascular monitoring devices 110 in a manner similar to the operation of a multi-function digital sports/fitness watch. Alternatively, the control mechanism 120 may be structurally combined with one of the cardiovascular monitoring devices 110, such as a cardiovascular monitoring device 110 coupled to the subject's arm.

The example embodiments allow frequent monitoring of the subject and can collect data continuously over extended periods of time when the subject is in a non-clinical setting. To enhance the convenience of collecting such data in a non-clinical setting, the cardiovascular monitoring devices 110 may have non-invasive and non-intrusive configurations. In particular, the cardiovascular monitoring devices 110 may be sufficiently small, discreet, and low-power to be compatible with wearable form factors that allow the subject to conduct different activities during data collection. In general, the example system 100 is configured so that the cardiovascular monitoring devices 110 can be coupled securely to, and removed from, respective body parts in a convenient and easy manner.

To supplement the cardiovascular data collected by the cardiovascular monitoring devices 110, the example system 100 may also include supplemental monitoring devices 130 that collect and transmit other types of data to the controller 120. The data from these supplemental monitoring devices 130 may help provide greater context for assessing the cardiovascular data. For instance, example system 100 may include other types of health data sensors 130 to collect health data 30a. The health data sensors 130a, for example, may include body temperature sensors, electroencephalography (EEG) sensors or galvanic skin response (GSR)/skin conductance/electrodermal activity (EDA) sensors, etc.

Additionally or alternatively, the example system 100 may include one or more motion sensors 130b, which include inertial measurement units (IMUs), accelerometers, or the like. For instance, by collecting data 30b on the movement of the subject and various body parts, for instance, a physician can determine the subject's activity during collection of the cardiovascular data in a non-clinical setting.

Additionally or alternatively, the example system 100 may include environmental sensors 130c that provide useful environmental data 30c that may relate to the subject's location, surroundings, and/or the subject's interaction with surrounding objects. For instance, the environmental sensors 130c may include a thermometer to record air temperature during data collection. The environmental sensors 130c may also include a global positioning system (GPS) to capture changes of location as the subject engages in the activity. For instance, by considering GPS data with the motion data, the physician can determine that the subject was taking a walk in the neighborhood and can assess how the subject's pace may indicate the state of the subject's cardiovascular health.

As shown in FIG. 1, the controller 120 may also be configured to transmit the data from the monitoring devices 110, 130 to an external system 140, such as a computer or cloud data storage, where for example a physician can access the data for analysis. The controller 120 may transmit the data to the external system 140 over a wide-area network (WAN), such as the Internet. The controller 120 may also transmit the data over a short distance to the external system over a wired or wireless connection. For example, the controller 120 may connect with the external system 140 using BLUETOOTH® or BLUETOOTH® LOW ENERGY (BLE) technology via the communication interface 124. In alternative embodiments, the data can be transmitted directly from the monitoring devices 110, 130 via the respective communication interfaces to the external system 140 over similar wired or wireless connections.

III. Example Embodiments for Processing Collected Data

As described above, the cardiovascular monitoring devices 110 may be coupled to different parts of the subject's body. For instance, the ECG sensor 110a may be coupled to the subject's chest; the PPG sensor 110b may be coupled to the subject's finger or forehead; and the Doppler ultrasound sensor 110c, the LDF sensor 110d, or the LSI sensor 110e may be coupled to the subject's arm or leg. These body parts might move during data collection. Indeed, the subject is likely to move these body parts in a non-clinical setting, especially during extended periods of continuous data collection where the subject might conduct everyday activities.

Motion of the body parts, however, can introduce motion-related artifacts into the collected data. In other words, during data collection, the cardiovascular monitoring devices 110 may detect signals attributable to the motion of the body parts. Motion-related artifacts may depend on the type of monitoring device 110 as well as the specific motion by the respective body part. Motion-related artifacts may obscure, distort, or misrepresent the actual cardiovascular data. Unless the motion-related artifacts can be identified and filtered from the collected data, the collected data may not provide accurate information about cardiovascular function.

In addition to motion-related artifacts, the data collected by the monitoring devices 110 may include other types of artifacts. As used herein, the term artifacts may refer broadly to any type of error, noise, or interference. In some cases, for instance, if a cardiovascular monitoring device 110 is not properly or securely coupled to a body part, the cardiovascular monitoring device 110 may not detect a consistently strong signal for measurement. In other cases, the signal for measurement may be inherently weak due to the configuration of the cardiovascular monitoring device 110 or the measurement technology involved.

A greater number of artifacts may be introduced as data is collected continuously over longer periods of time. When artifacts are introduced, any attempt to collect data continuously over an extended period of time may not provide sufficiently accurate data for correct assessment of cardiovascular function.

Additionally, examining the pulsatile behavior of the cardiovascular system may involve making rapid measurements over the course of the cardiac cycle. For instance, with these rapid measurements, systolic and diastolic blood pressures or arterial flow rates versus time can be evaluated. Rapid changes in data are more difficult to identify and assess when artifacts are present. Smaller, but perhaps significant, details in the rapid measurements may be obscured by artifacts.

The example system 100 can process the collected data to allow cardiovascular function to be accurately evaluated, even if the collected data may include measurements of artifact signals. In particular, the example system 100 collects data simultaneously from the multiple cardiovascular monitoring devices 110 during the same period of time. The data from these cardiovascular monitoring devices 110 are based on measurements of indicators resulting from the same cardiac activity. The data from the cardiovascular monitoring devices 110 include components that are attributable to common aspects of the same cardiac activity. As such, the data include components that are correlated. By statistically comparing the data collected from the multiple cardiovascular monitoring devices 110 during the same time period, the example system 100 can identify the correlated components which are attributable to cardiovascular function.

Figure 3:
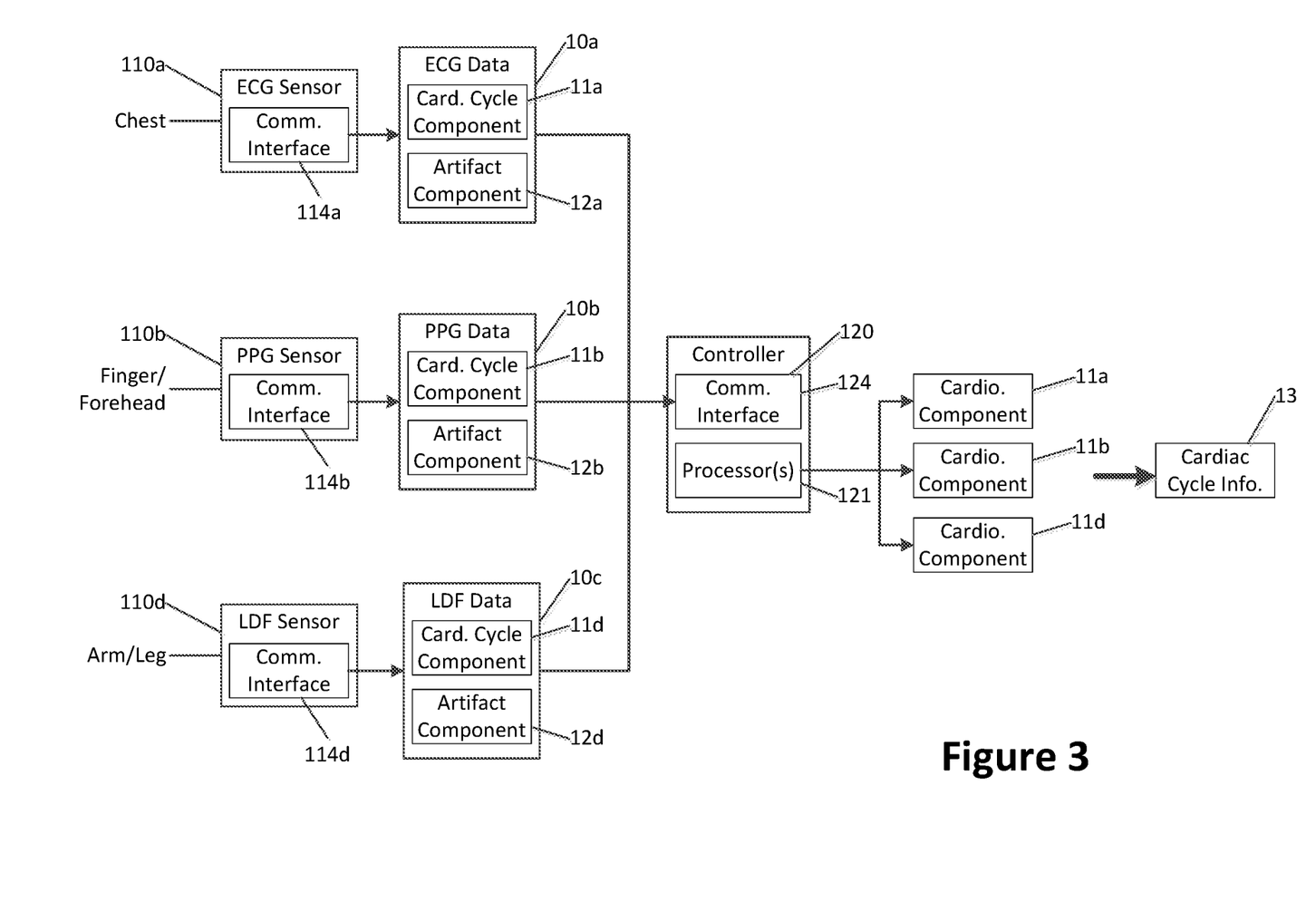
FIG. 3 illustrates an example system employing multiple monitoring devices where the data from the monitoring devices are processed to identify correlated components relating to cardiovascular function and to reject uncorrelated artifact components, according to aspects of the present disclosure.

FIG. 3 illustrates an example embodiment, where the ECG sensor 110a, the PPG sensor 110b, and the LDF sensor 110d may be operated to collect the ECG data 10a, the PPG data 10b, and the LDF data 10d simultaneously over a given time period. In alternative embodiments, the Doppler ultrasound sensor 110c or the LSI sensor 110e may be employed in place of the LDF sensor 110d to collect data relating to blood flow. As shown in FIG. 3, the ECG data 10a, the PPG data 10b, and the LDF data 10d are transmitted to the communication interface 124 of the controller 120 via respective communication interfaces 114a, b, d.

Because the data 10a, b, d are collected by the sensors 110a, b, d during the same period of time, the data 10a, b, d result from the same cardiovascular activity. In particular, the data 10a, b, d relate respectively to electrical activity, changes in blood volume, and changes in blood flow that occur over the same repeating cardiac cycles, e.g., pulsatile waveforms. As such, the data 10a, b, d each include respective components 11a, b, d that are attributable to the same underlying cardiac cycles. Furthermore, because the components 11a, b, d are attributable to the same cardiac cycles, the components 11a, b, d are correlated.

In addition to the cardiac cycle components 11a, b, d, however, the data 10a, b, d may also include respective artifact components 12a, b, d. For instance, when the sensors 110a, b, d measure signals from the respective body parts to collect the data 10a, b, d, the sensors 110a, b, d may each experience movement, interference, and/or other phenomena that produce artifacts in the measured signals.

In contrast to the correlated cardiac cycle components 11a, b, d, the artifact components 12a, b, d may generally be the result of different respective phenomena. Accordingly, the artifact components 12a, b, d are generally uncorrelated. For instance, motion-related artifacts for the sensors 110a, b, d may be caused by different motions by the different respective body parts. The ECG sensor 110a may detect artifact signals from movement of the chest; the PPG sensor 110b may detect artifact signals from movement of the finger or forehead; and the LDF sensor 110d may detect artifact signals from movement of the arm or leg. Additionally, artifacts may also result from the operation of a particular type of sensor and the specific type of technology used by that sensor.

Information 13 relating to the cardiac cycles can be determined by extracting the correlated cardiac cycle components 11a, b, d from the data 10a, b, d. The cardiac cycle information 13 may provide a pulsatile waveform. In addition, because the artifact components 12a, b, d are generally uncorrelated, the process of extracting the correlated cardiac cycle components 11a, b, d also results in the rejection of the uncorrelated artifact components 12a, b, d. To extract the correlated cardiac cycle components 11a, b, d, the processor(s) 121 of the controller 120, for instance, can process the data 10a, b, d according to power spectrum analysis, primary component analysis (PCA), and/or independent component analysis (ICA).

Once the cardiac cycle information 13 has been accurately determined from the cardiac cycle components 11a, b, d, the cardiac cycle information 13 can be employed to analyze the ECG data 10a, PPG data 10b, and the LDF data 10d further. In other words, the measurements of electrical activity, changes in blood volume, and/or blood flow can be more accurately evaluated with accurate information on the underlying cardiac cycles.

The cardiac cycle information 13 can be employed to improve the calculations of other cardiovascular indicators. For instance, pulse transit time (PTT) and pulse wave velocity (PWV) may be used to estimate arterial stiffness in an assessment of cardiovascular health. The PTT and the PWV can be determined from the ECG data 10a and the PPG data 10b. In particular, the PTT and the PWV may be determined by evaluating cyclic peak times in waveforms corresponding to the ECG data 10a and the PPG data 10b. Evaluation of the ECG data 10a and the PPG data 10b can be achieved with greater accuracy due to the accurate identification of the underlying cardiac cycle in the information 13. In turn, the PTT and the PWV can be more accurately calculated.

As shown in FIG. 3, the data 10a, b, d from the three respective sensors 110a, b, d are employed to extract the cardiac cycle information 13. Example systems, however, may employ any combination and any number (e.g. two, four, five, etc.) of sensors to identify correlated components relating to cardiac activity and to remove artifact components from consideration.

In the example embodiments described above, the ECG sensor 110a may be coupled to the subject's chest; the PPG sensor 110b may be coupled to the subject's finger or forehead; and the Doppler ultrasound sensor 110c, the LDF sensor 110d, or the LSI sensor 110e may be coupled to the subject's arm or leg. Thus, some embodiments may employ a plurality of monitoring devices where each sensor is coupled to a different respective body part and measures a different respective type of signal (e.g., a first type of sensor to measure electrical activity at a chest, a second type of sensor to measure blood volume at a finger, and a third type of sensor to measure blood flow at an arm). Other configurations of monitoring devices, however, may also be employed to collect data for accurate assessment of cardiovascular function according to aspects of the present disclosure. For instance, a plurality of monitoring devices in other embodiments may include at least a first sensor configured to measure a first type of signal at a first body part and a second sensor configured to measure a second type of signal at the first body part, where the first type of signal is different from the second type of signal (e.g., a first type of sensor to measure blood volume at a finger and a second type of sensor at the same finger to measure blood flow). Meanwhile, a plurality of monitoring devices in yet other embodiments may include at least a first sensor configured to measure a first type of signal at a first body part and a second sensor configured to measure the first type of signal at a second body part, where the first body part is different from the second body part (e.g., the same type of sensor to measure blood flow at an arm and a leg).

Furthermore, as described above, other configurations of monitoring devices may use cardiovascular sensors in combination with the supplemental monitoring devices 130 which may collect other types of data. For instance, example systems may employ motion sensors 130b, which include inertial measurement units (IMUs), accelerometers, or the like. The motion sensors 130b may be coupled to body parts to detect motion by the body parts, where the motion may generate motion-related artifacts at cardiovascular sensors. Thus, information from the motion sensors 130b can be used to help identify and reject motion-related artifacts when processing data collected by cardiovascular sensors.

Figure 4:
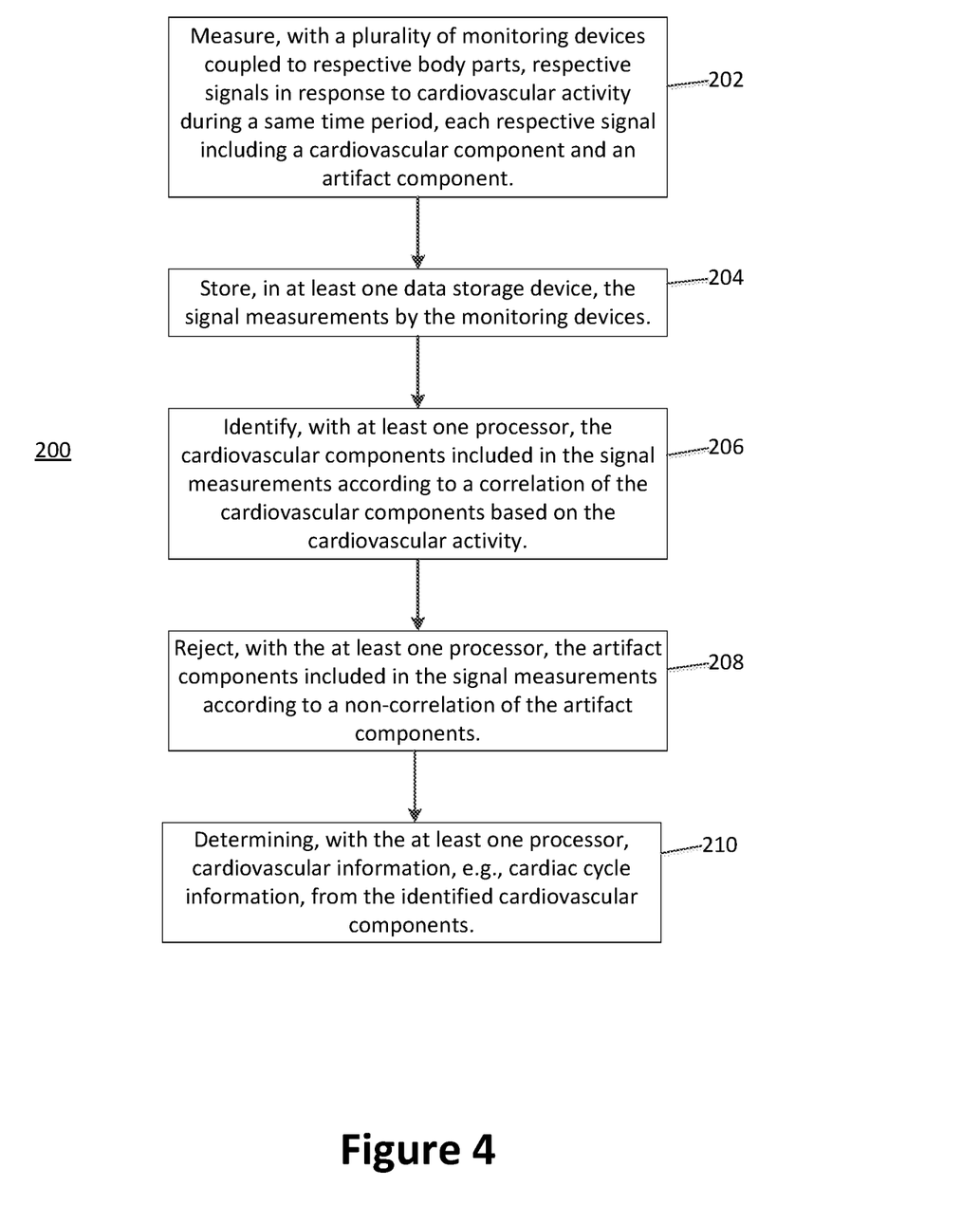
FIG. 4 illustrates an example method for processing collected data to identify correlated components relating to cardiovascular function and to reject uncorrelated artifact components, according to aspects of the present disclosure.

FIG. 4 illustrates an example method 200 for collecting and processing cardiovascular data. A plurality of monitoring devices is coupled to different respective body parts of a subject. In step 202, each monitoring device measures a respective signal at the respective body part in response to cardiovascular activity occurring during a same time period. The respective signal includes a cardiovascular component attributable to the cardiovascular activity and an artifact component not attributable to the cardiovascular activity. In step 204, at least one data storage device stores the signal measurements by the monitoring devices. In step 206, at least one processor identifies the cardiovascular components in the signal measurements according to a correlation of the cardiovascular components based on the common cardiovascular activity. In step 208, the at least one processor rejects the artifact components according to a non-correlation of the artifact components. In step 210, the at least one processor determines cardiovascular information, e.g., cardiac cycle information, from the identified cardiovascular components.

Figure 5:
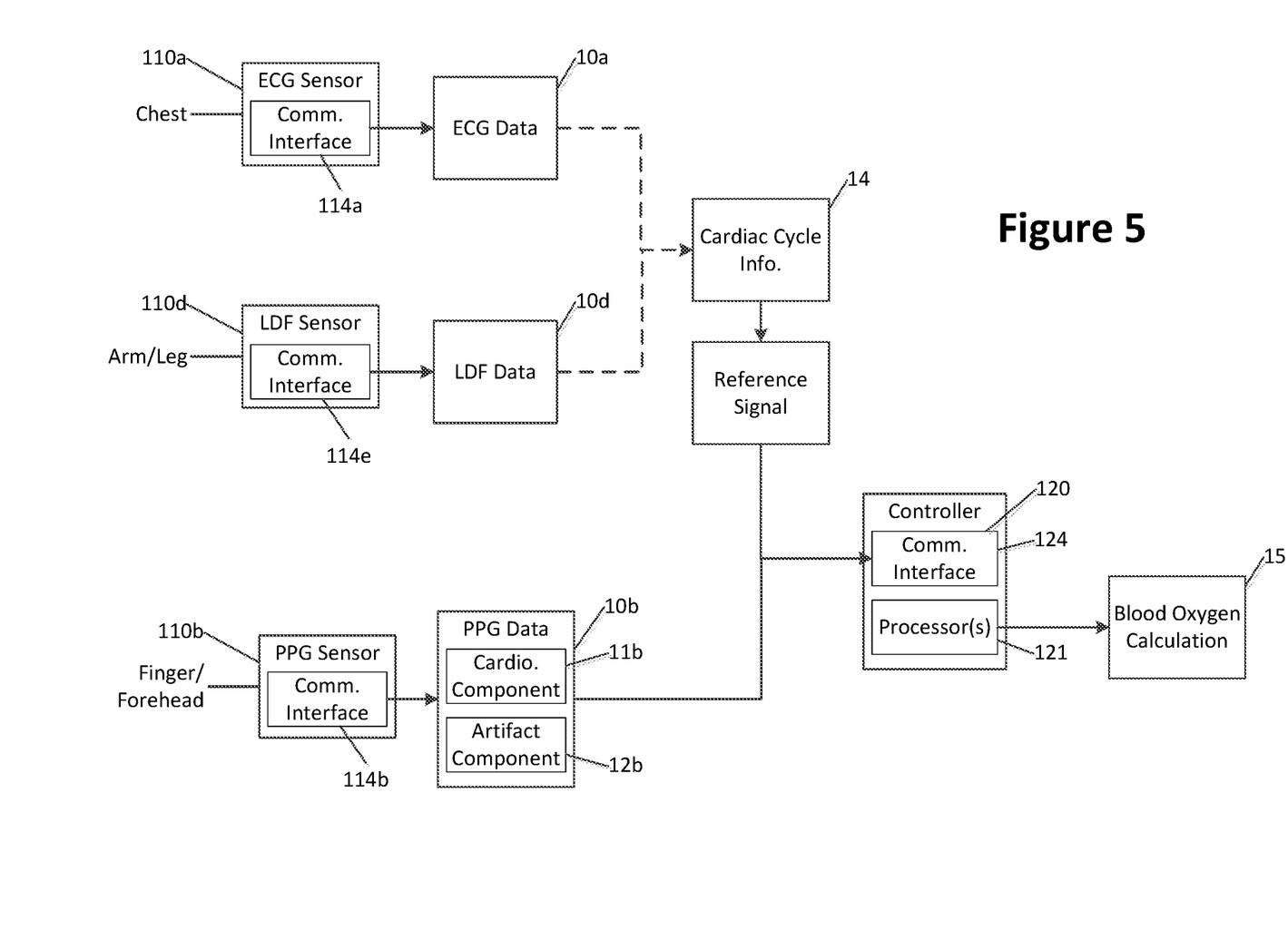
FIG. 5 illustrates an example system employing multiple monitoring devices to collect and process data relating to cardiovascular function, according to aspects of the present disclosure.

According to additional embodiments, one or more monitoring devices may be employed to accurately determine cardiac cycle information, and the cardiac cycle information can be used as a reference signal to process data collected by another monitoring device. FIG. 5 illustrates another example embodiment, where the ECG sensor 110a, the PPG sensor 110b, and the LSI sensor 110e may be operated to collect the ECG data 10a, the PPG data 10b, and the LSI data 10e simultaneously over a given time period. The ECG data 10a and/or the LSI data 10e may be employed to determine cardiac cycle information 14 for the data collection period. For instance, to determine the cardiac cycle information 14, correlated components relating to the underlying cardiac cycle may be extracted from the data 10a, e as described above.

The cardiac cycle information 14 can then be used to provide a reference signal for processing the PPG data 10b from the PPG sensor 110b. In particular, the cardiac cycle information 14 may be employed to identify the component 11b of the PPG data 10b attributable to cardiovascular function and to distinguish the component 11b from any variance due to artifacts reflected in the component 12b.

As described above, the PPG sensor 110b may employ a pulse oximeter, which includes a light source, such as an LED, and a photodetector, such as a photodiode. The pulse oximeter can be used to determine oxygen level (or oxygen saturation) in the blood. Blood oxygenation may be calculated by taking measurements with the pulse oximeter at multiple wavelengths and identifying the DC and AC components of the measurements. This involves an accurate calculation of the signal variation over the cardiac cycle apart from the effect of any artifacts. As such, using the cardiac cycle information 14 allows these signal variations to be accurately identified.

Figure 6:
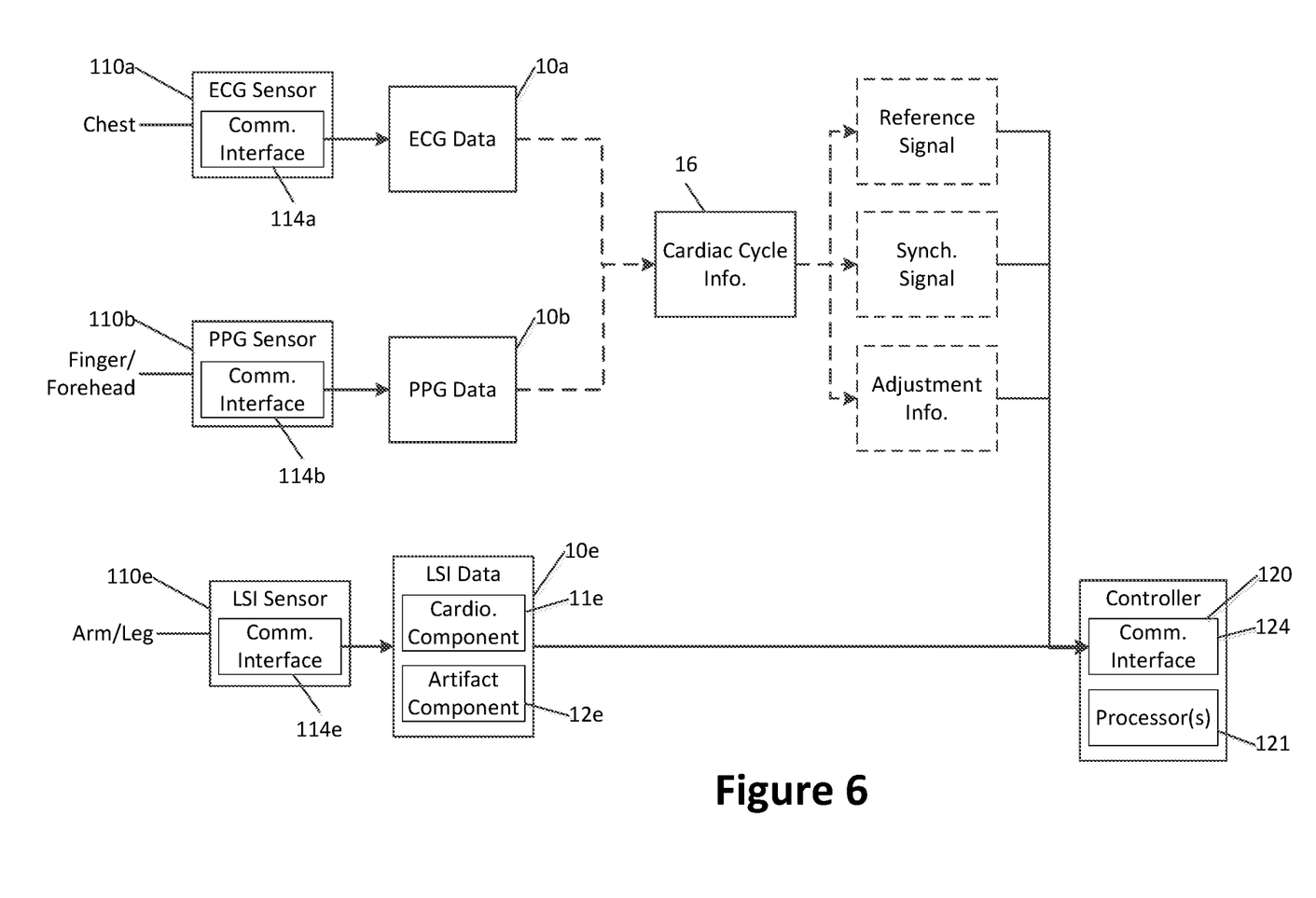
FIG. 6 illustrates another example system employing multiple monitoring devices to collect and process data relating to cardiovascular function, according to aspects of the present disclosure.

In this example, to calculate blood oxygen level 15, the analysis of PPG data 10b employs the reference signal generated from the ECG data 10a and/or the LSI data 10e. In general, however, data from a monitoring device 110 may be processed according to a reference signal generated from data provided by other monitoring device(s). Thus, as shown in FIG. 6, an alternative embodiment may use a reference signal based on cardiac cycle information 16 generated from the ECG data 10a and/or the PPG data 10b to analyse the LSI data 10e.

According to alternative embodiments, one or more monitoring devices may be employed to accurately determine cardiac cycle information, and this cardiac cycle information can be used to synchronize data collected by another monitoring device. Thus, referring again to FIG. 6, the cardiac cycle information 16 can be used to synchronize the LSI data 10e. For instance, the measurements of blood flow by the LSI sensor 110e include natural variations over a single cardiac cycle. The assessment of blood pressure from these measurements involves identifying the systolic and diastolic pressures occurring at different times within the cardiac cycle. To allow such information within each cardiac cycle to be evaluated, the measurements cannot be averaged over the cardiac cycle. However, the phase of the measurements from the LDF sensor 110e can be synchronized with the separately determined cardiac cycle information 16.

According to yet further embodiments, one or more monitoring devices may be employed to accurately determine cardiac cycle information, and this cardiac cycle information can be used to optimize, calibrate, or otherwise adjust how data is collected by another monitoring device. Thus, referring again to FIG. 6, the cardiac cycle information 16 generated from the ECG data 10a and/or the PPG data 10b can be used to optimize or calibrate measurements by the LSI sensor 110e. The sensitivity of LSI sensor 110e to blood flow velocity depends on sensor exposure time. Using the cardiac cycle information 16, the sensor exposure for the LSI sensor 110e may be varied until an optimal correlation is achieved between the LSI data 10e from the LSI sensor 110e and the cardiac cycle information 16, enabling optimization of system parameters for greater LSI sensitivity. Similarly, measurements may be used to adjust analog or digital electrical filters, or computational processing parameters.

In general, data collected by one or more monitoring devices may be employed to guide the collection of data by another monitoring device. In a further embodiment, for instance, a signal from a first monitoring device coupled to a body part may confirm the presence of vasculature for the subsequent collection of other data by a second monitoring device at the same body part. Alternatively, cardiac cycle information may be generated from data collected by a first monitoring device, and based on this cardiac cycle information, a second monitoring device is configured to make measurements at only an intended phase within the cardiac cycle (peak systolic, for instance). By selectively triggering the operation of the second monitoring device based on data from the first monitoring device, resources, such as electrical power or computational resources, for operating the second monitoring device can be conserved.

IV. Conclusion

In view of the foregoing, example systems can robustly and accurately collect data relating to a subject's cardiovascular function. The example systems may include monitoring devices that measure signals relating to pulse, blood flow, blood pressure, and/or other indicators of cardiovascular function. The example systems can extract cardiovascular data from the measurements and separate the cardiovascular data from artifacts, which may obscure, distort, or misrepresent data relating to the cardiovascular function. The extracted cardiovascular data, e.g., cardiac cycle information, can then be used for further accurate assessment of the cardiovascular function.

The embodiments described herein employ devices for processing information and controlling aspects of the example systems, e.g., the controller 120. Such devices may be implemented as a combination of hardware and software elements. The hardware elements may include combinations of operatively coupled hardware components, including microprocessors, memory, signal filters, circuitry, etc. The processors may be configured to perform operations specified by the software elements, e.g., computer-executable code stored on computer readable medium. The processors may be implemented in any device, system, or subsystem to provide functionality and operation according to the present disclosure. The processors may be implemented in any number of physical devices/machines. Indeed, parts of the processing of the example embodiments can be distributed over any combination of processors for better performance, reliability, cost, etc.

The physical devices/machines can be implemented by the preparation of integrated circuits or by interconnecting an appropriate network of conventional component circuits, as is appreciated by those skilled in the electrical art(s). The physical devices/machines, for example, may include field programmable gate arrays (FPGA's), application-specific integrated circuits (ASIC's), digital signal processors (DSP's), etc.

Appropriate software can be readily prepared by programmers of ordinary skill based on the teachings of the example embodiments, as is appreciated by those skilled in the software arts. Thus, the example embodiments are not limited to any specific combination of hardware circuitry and/or software. Stored on one computer readable medium or a combination of computer readable media, the computing systems may include software for controlling the devices and subsystems of the example embodiments, for driving the devices and subsystems of the example embodiments, for enabling the devices and subsystems of the example embodiments to interact with a human user (user interfaces, displays, controls), etc. Such software can include, but is not limited to, device drivers, operating systems, development tools, applications software, etc. A computer readable medium further can include the computer program product(s) for performing all or a portion of the processing performed by the example embodiments. Computer program products employed by the example embodiments can include any suitable interpretable or executable code mechanism, including but not limited to complete executable programs, interpretable programs, scripts, dynamic link libraries (DLLs), applets, etc. The processors may include, or be otherwise combined with, computer-readable media. Some forms of computer-readable media may include, for example, a hard disk, any other suitable magnetic medium, any suitable optical medium, RAM, PROM, EPROM, flash memory, any other suitable memory chip or cartridge, any other suitable non-volatile memory, a carrier wave, or any other suitable medium from which a computer can read.

The processing/control devices may also include databases for storing data. Such databases may be stored on the computer readable media described above and may organize the data according to any appropriate approach. For examples, the data may be stored in relational databases, navigational databases, flat files, lookup tables, etc.

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A system for collecting data for assessment of cardiovascular function, comprising:

a plurality of cardiovascular monitoring devices configured to be coupled to body parts of a subject and to determine cardiovascular signal measurements at the body parts in response to cardiovascular activity, each monitoring device including a respective first communication interface and configured to determine a respective one of the cardiovascular signal measurements at a respective one of the body parts in response to the cardiovascular activity, the cardiovascular signal measurements including cardiovascular components attributable to the cardiovascular activity and artifact components not attributable to the cardiovascular activity, the artifact components being attributable at least to movement of at least one of the body parts, wherein the plurality of cardiovascular monitoring devices includes at least two of: (i) a first sensor configured to measure electrical signals in response to the cardiovascular activity, (ii) a second sensor configured to measure blood volume in response to the cardiovascular activity, or (iii) a third sensor configured to measure blood flow in response to the cardiovascular activity, and wherein, in response to the plurality of cardiovascular monitoring devices determining the cardiovascular signal measurements at the body parts simultaneously over a same time period, the cardiovascular components included in the cardiovascular signal measurements by the cardiovascular monitoring devices are correlated and the artifact components included in the cardiovascular signal measurements by the cardiovascular monitoring devices are not correlated; and a controller including:
  a second communication interface configured to be communicatively coupled to the first communication interface of each monitoring device;
  at least one data storage device; and
  at least one processor configured to: (i) receive the cardiovascular signal measurements from the cardiovascular monitoring devices via the second communication interface; (ii) store the cardiovascular signal measurements on the at least one data storage device; (iii) determine a correlation of the cardiovascular components and a non-correlation of the artifact components by statistically comparing the cardiovascular signal measurements from the plurality of cardiovascular monitoring devices; (iv) identify the cardiovascular components included in the cardiovascular signal measurements according to the correlation of the cardiovascular components; (v) reject the artifact components included in the cardiovascular signal measurements according to the non-correlation of the artifact components; and (vi) determine cardiovascular information from the cardiovascular components separated from the artifact components for an assessment of cardiovascular function, wherein the at least one processor rejects the artifact components attributable to the movement of at least one of the body parts based on the cardiovascular signal measurements from the at least two of the first sensor, the second sensor, or the third sensor and without a measurement from an accelerometer.

2. The system according to claim 1, wherein the plurality of cardiovascular monitoring devices includes at least a first sensor configured to measure a first type of signal at a first body part and a second sensor configured to measure a second type of signal at a second body part, the first type of signal being different from the second type of signal and the first body part being different from the second body part.

3. The system according to claim 1, wherein the first sensor includes an electrocardiography (ECG) sensor, the second sensor includes a photoplethysmography (PPG) sensor, and the third sensor includes at least one of a Doppler ultrasound sensor, a laser Doppler flowmetry (LDF) sensor, or a laser speckle imaging (LSI) sensor.

4. The system according to claim 1, wherein each monitoring device is configured to determine the respective one of the cardiovascular signal measurements at the respective one of the body parts in response to cardiovascular activity over a plurality of cardiac cycles during the same time period,
the cardiovascular component of the signal measurement includes data relating to the plurality of cardiac cycles, and
the at least one processor of the controller is configured to identify the data relating to the plurality of cardiac cycles included in the cardiovascular signal measurements and to determine cardiac cycle information for the assessment of cardiovascular function.

5. The system according to claim 1, further comprising motion sensors configured to collect motion data in response to motion by at least some of the body parts.

6. A method for collecting data for assessment of cardiovascular function, comprising:
determining, with each of a plurality of cardiovascular monitoring devices coupled to body parts of a subject, cardiovascular signal measurements at the body parts in response to cardiovascular activity during a same time period, each monitoring device including a respective first communication interface and configured to determine a respective one of the cardiovascular signal measurements at a respective one of the body parts in response to the cardiovascular activity, the cardiovascular signal measurements including cardiovascular components attributable to the cardiovascular activity and artifact components not attributable to the cardiovascular activity, the artifact components including an artifact attributable to movement of at least one of the body parts,
wherein the plurality of cardiovascular monitoring devices includes at least two of: (i) a first sensor configured to measure electrical signals in response to the cardiovascular activity, (ii) a second sensor configured to measure blood volume in response to the cardiovascular activity, or (iii) a third sensor configured to measure blood flow in response to the cardiovascular activity;
storing, in at least one data storage device, the cardiovascular signal measurements determined by the plurality of cardiovascular monitoring devices;
determining a correlation of the cardiovascular components and a non-correlation of the artifact components by statistically comparing the cardiovascular signal measurements from the plurality of cardiovascular monitoring devices;
identifying, with at least one processor, the cardiovascular components included in the cardiovascular signal measurements according to the correlation of the cardiovascular components;
rejecting, with the at least one processor, the artifact components included in the cardiovascular signal measurements according to the non-correlation of the artifact components; and
determining, with the at least one processor, cardiovascular information from the cardiovascular components separated from the artifact components,
wherein rejecting the artifact components includes rejecting the artifact components attributable to the movement of at least one of the body parts based on the cardiovascular signal measurements from the at least two of the first sensor, the second sensor, or the third sensor and without a measurement from an accelerometer.

7. The method according to claim 6, wherein the first sensor includes an electrocardiography (ECG) sensor, the second sensor includes a photoplethysmography (PPG) sensor, and the third sensor includes at least one of a Doppler ultrasound sensor, a laser Doppler flowmetry (LDF) sensor, or a laser speckle imaging (LSI) sensor.

8. The method according to claim 6, wherein determining the respective one of the cardiovascular signal measurements with each monitoring device includes determining the respective one of the cardiovascular signal measurements at the respective one of the body parts in response to the cardiovascular activity over a plurality of cardiac cycles during the same time period, the cardiovascular components of the cardiovascular signal measurements including data relating to the plurality of cardiac cycles,
identifying the cardiovascular components includes identifying the data relating to the plurality of cardiac cycles according to the correlation, and
determining cardiovascular information includes determining cardiac cycle information for the assessment of cardiovascular function.

* * * * *